United States Patent
Thaper et al.

(10) Patent No.: US 6,541,511 B1
(45) Date of Patent: Apr. 1, 2003

(54) METHYL ANALOGS OF SIMVASTATIN AS NOVEL HMG-COA REDUCTASE INHIBITORS

(75) Inventors: Rajesh Kumar Thaper, Hidersbad (IN); Saridi Madhava Dileep Kumar, Andhra Pradesh (IN); Yatendra Kumar, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/166,468

(22) Filed: Jun. 10, 2002

(30) Foreign Application Priority Data

Jun. 12, 2001 (IN) ........................................ 659/Del/2001

(51) Int. Cl.$^7$ ........................ A61K 31/35; A61K 31/215
(52) U.S. Cl. ........................ 514/460; 514/529; 549/292; 560/129
(58) Field of Search .................. 549/292; 514/460, 514/529; 560/129

(56) References Cited

FOREIGN PATENT DOCUMENTS

| | | |
|---|---|---|
| EP | 0 052 366 | 5/1982 |
| EP | 0 068 038 | 9/1985 |
| GB | 1555831 | 11/1979 |
| GB | 2055100 | 2/1981 |
| GB | 2073199 | 10/1981 |

OTHER PUBLICATIONS

Hoffman et al., "3–Hydroxy–3–methylglutaryl–coenzyme A Reductase Inhibitors. 4. Side Ester Derivatives of Mevinolin" *J. Med. Chem*, 1986; 29: 849–852.

Stokker, Gerald E., "Synthesis of L–669,262, a Potent HMG–CoA Reductase Inhibitor" *J. Org. Chem*, 1994; 59: 5983–5986.

Lee et al., "Structural Modification of Mevinolin" *J. Org. Chem.* 1982; 47: 4750–4757.

*Primary Examiner*—Amelia Owens
(74) *Attorney, Agent, or Firm*—Jayadeep R. Deshmukh

(57) ABSTRACT

The present invention relates to a novel methyl analog of simvastatin, which has the ability to inhibit the synthesis of cholesterol. The compound of the present invention holds promise for the treatment and prophylaxis of hypercholesterolemia and of various cardiac disorders. The invention also relates to a process for making the novel compound.

22 Claims, No Drawings

METHYL ANALOGS OF SIMVASTATIN AS NOVEL HMG-COA REDUCTASE INHIBITORS

FIELD OF THE INVENTION

The present invention relates to a novel methyl analog of simvastatin, which has the ability to inhibit the synthesis of cholesterol. The compound of the present invention holds promise for the treatment and prophylaxis of hypercholesterolemia and of various cardiac disorders. The invention also relates to a process for making the novel compound.

BACKGROUND OF THE INVENTION

Hypercholesterolemia is a known primary risk factor for the progression of atherosclerosis. High serum cholesterol is regarded as a major risk factor for the development of ischaemic heart disease and there is, therefore, a need for drugs which have the effect of reducing the blood cholesterol levels.

Over the past several years a number of structurally related anti-hypercholesterolemic agents acting by inhibition of 3-hydroxy-3-methylglutaryl-coenzyme (HMG-CoA) reductase have been developed and are now commercially available. The compounds have varied from the natural fermentation products, compactin of structural formula I

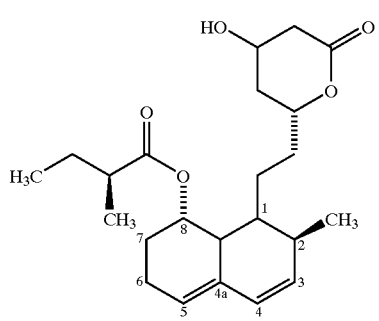

FORMULA-I and mevinolin of structural formula II

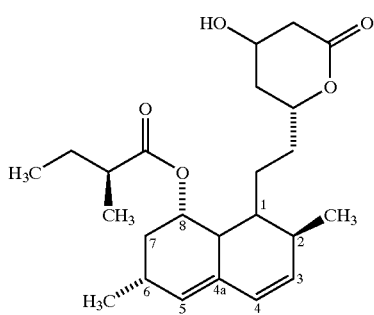

FORMULA-II (GB 1,555,831; 2,055,100; 2,073,199) to di- and tetrahydro derivatives thereof (EP 0,052,366); to analogs with different esters in the 8-position of the polyhydronaphthalene moiety, to totally synthetic analogs, wherein the polyhydronaphthalene moiety is replaced by substituted mono-and bicylic aromatics, and biphenyls (EP 0,068,038). In all of these compounds, the homochiral β-hydroxypyranone ring of structural formula III

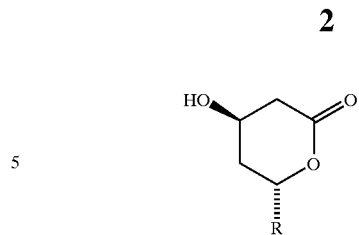

FORMULA-III or its corresponding ring—opened dihydroxy acid of structural formula IV

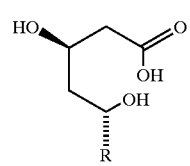

FORMULA-IV was preserved, thereby establishing it as a key structural feature responsible for its HMG-CoA reductase inhibitory activity. Soon afterwards, intense efforts were directed to the design and development of synthetic strategies for selectively modifying the side-chain ester and the lactone moieties of mevinolin.

Analogs of mevinolin by the modification of the 2(S)-methylbutyryl side chain and hexahydronaphthalene nucleus have been extensively studied (W. F. Hoffman et. al J. Med. Chem. 1986; 29: 849 and Gerald E. Stokker, J. Org. Chem. 1994; 59: 5983). These studies led to a series of side chain ester derivatives, the new analogs with more pronounced or reduced activity e.g. simvastatin, which has an extra methyl group in the methylbutyryl side chain and is twice as potent as mevinolin.

Synthetic strategies for modifying the side chain ester and lactone moieties of mevinolin have been described by Ta-Jyh-Lee in J. Org. Chem. 1982; 47: 4750. Mevalonate analogs of structural formula V and VI by substituting hydroxy bearing carbon in the HMG-CoA and mevinolinic acid with a methyl group have been prepared.

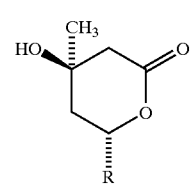

FORMULA-V

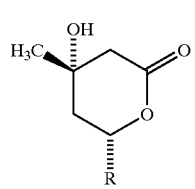

FORMULA-VI

However, mevalonate analogs with a methyl group at the 3-position of the β-hydroxypyranone ring has not been reported in the literature.

SUMMARY OF THE INVENTION

The present invention relates to a novel methyl analog of simvastatin, having HMG-CoA reductase inhibitor activity.

The compound of this invention possesses a methyl group in both the orientation (R) and (S), substituted at the 3-position of the β-hydroxypyranone ring. These may be in the lactone or corresponding dihydroxy acid forms (closed or open).

In the hydrophobic bonding which accounts for the major part of drug receptor bond energy, the methyl groups in a drug molecule plays an important role. However, the biological consequences of methyl groups in the β-hydroxypyranone ring position of statins have been rarely studied.

An object of the present invention is to provide a novel compound that exhibits significant HMG-CoA reductase inhibitory activity. Accordingly, the present invention provides a compound having the Formula VII,

FORMULA-VII

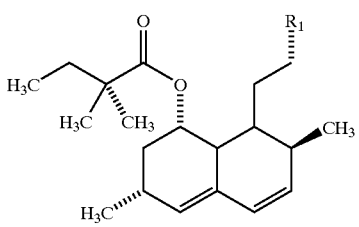

wherein $R_1$ is a β-hydroxypyranone ring, of structural formulae VIIa–d

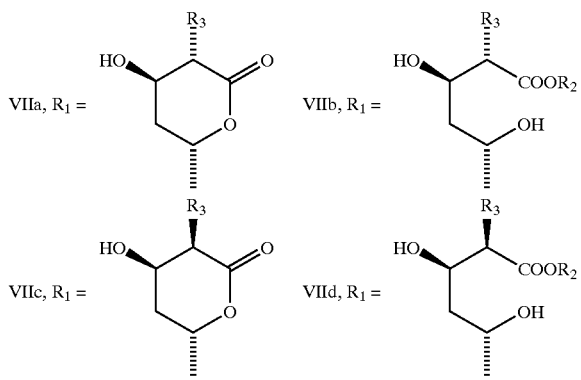

wherein $R_2$ is Na, K or $NH_4$; $R_3$ is a methyl group, and its pharmaceutically acceptable salts.

Another object of the present invention is to provide a process for the preparation of said HMG-CoA reductase inhibitor, which comprises reacting simvastatin of Formula VIIIa, which is the lactone form, or of Formula VIIIb, which is the open ring hydroxy acid form, FORMULA-VIIIa

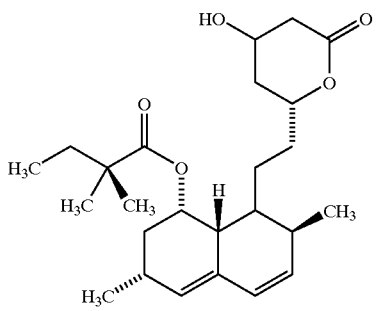

FORMULA-VIIIb

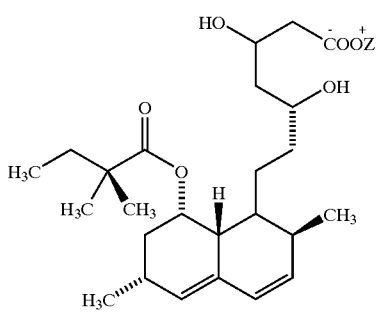

wherein Z is hydrogen, a metal cation, such as Na, K or $NH_4$, with a methylating agent.

A solution of simvastatin is reacted with a methylating agent in the presence of a base at a temperature from about −10° C. to about −60° C. under an atmosphere of nitrogen followed by a suitable aqueous work up and crystallization from organic solvents.

The methylating agent used is an alkyl halide, such as methyl iodide. The base required is used in the form of an alkali metal salt, like lithium pyrrolidide or lithium hexamethyldisilazane (Li-HMDS). Lithium pyrrolidide is generated in situ by the reaction of n-butyl lithium with pyrrolidine in tetrahydrofuran.

The methylation of α-methylene site in the pyranone ring is achieved via ester enolate formed with bases like hexamethyldisilazane (Li-HMDS) or lithium pyrrolidide. Enolization with lithium pyrrolidone during methylation afforded a mixture of (3R) and (3S) isomers of structural formulae (VIIc) and (VIIa), respectively. This low stereoselectivity using lithium pyrrolidone may be attributed to the lower bulk of pyrrolidone group allowing entry from both the faces of pyranone ring. However, due to more steric bulk of Li-HMDS it approaches the pyranone ring from less hindered side, and enolization with Li-HMDS followed by methylation led stereospecifically to the formation of (3R) methyl isomer of simvastatin of structural formula (VIIc).

The methylation reaction is preferably performed without protecting the two hydroxy groups of the open pyranone ring of simvastatin at a temperature from about −25° C. to about −55° C.

Suitable aqueous work-up involves the addition of water to the reaction mixture after the methylation is completed followed by an extraction with organic solvents. Any organic solvent may be used for the extraction and such solvents include water immisicible and partially miscible solvents such as chloroform, dichloromethane, 1,2-dichloroethane, hexanes, cyclohexane, toluene, methyl acetate, ethyl acetate, and the like. The organic phase is washed with a mineral acid to remove the basic impurities. The acids may include hydrochloric acid, sulfuric acid and phosphoric acid.

The product may be obtained by reducing the volume of the organic solvent containing the methyl analog of simvastatin by evaporation, adding a miscible polar solvent and precipitating the desired product by addition of an antisolvent. The addition of polar solvent greatly reduces the presence of impurities, in the final product. Polar solvent may be selected from the group consisting of a lower alkanol, denatured spirit, isopropanol and the like, ketones such as acetone or esters such as methyl acetate or ethyl acetate, and mixtures thereof. The precipitation may be effected by the addition of appropriate quantities of antisolvent and include water, alkanes, mixture of alkanes, such as hexane, cyclohexane or cyclopentane, ethers such as isopropyl ethers or aromatic hydrocarbons such as benzene or toluene. The polar solvent and the anti-solvent should be at least partially miscible and preferably completely miscible.

Methods known in the art may be used with the process of this invention to enhance any aspect of this process. The product (isomers) obtained may further be purified by any technique known to a person skilled in the art for example filtration, crystallization, column chromatography, preparative HPLC, TLC or a combination of these procedures.

The in vivo and in vitro biological activity of the methyl analog of simvastatin isomeric compounds of structural formulae VIIc and VIIa was carried out on a HMG-CoA reductase inhibitory model. The compounds were tested at three concentrations ($10^{-5}$, $10^{-7}$ and $10^{-9}$ M) for the in vitro activity.

The results indicated that the compound VIIc possesses significant HMG-CoA reductase inhibitory activity.

The in vivo experiments were conducted using radiolabelled ($^{14}C$) acetate which was administered to the rats converting it into ($^{14}C$) cholesterol. This synthesis was measured by quantitating ($^{14}C$) cholesterol inhibited by HMG-CoA reductase inhibitor. The in vivo results indicated that the compounds (VIIc) and (VIIa) have cholesterol lowering activity. The results of the above experiment have been summarized in Table 1 and Table 2.

TABLE 1

% HMG-CoA REDUCTASE INHIBITION ACTIVITY OF (VIIc) and (VIIa)

| Concentration | % Inhibition activity | |
| --- | --- | --- |
|  | (VIIc) | (VIIa) |
| $10^{-5}$ | 99 | 100 |
| $10^{-7}$ | 71 | 93 |
| $10^{-9}$ | 8 | 30 |

TABLE 2

IN VIVO INHIBITION OF ($^{14}C$) CHOLESTEROL PREPARED FROM $^{14}C$ ACETATE IN RATS

| Compound | Dose | % inhibition |
| --- | --- | --- |
| (VIIc) | 1 mg/kg orally | 0% |
|  | 1 mg/kg i.p. | 8% |
|  | 5 mg/kg orally | 57% |
| (VIIa) | 1 mg/kg orally | 0% |
|  | 1 mg/kg i.p. | 10% |
|  | 5 mg/kg orally | 69% |

DETAILED DESCRIPTION OF THE INVENTION

In the following section preferred embodiments are described by way of examples to illustrate the process of this invention. However, these are not intended in any way to limit the scope of the present invention.

EXAMPLE 1

6(R)-[2-[8(S)-[[2,2-Dimethylbutanoyl]oxy]-2(S),6(R)-dimethyl-1,2,6,7,8,8a(R)-hexahydro-1(S)-napthyl]ethyl]-3(S)-methyl,4(R)-hydroxy-3,4,5,6-tetrahydro-2H-pyran-2-one (VIIc)

To a solution of simvastatin (10 g, 0.023 mol) in tetrahydrofuran (130 ml), lithium hexadimethylsilazane (1.3 M in hexane, 55.14 ml, 0.05 mol) was added through a syringe maintaining temperature at −40 to −45° C. under an atmosphere of nitrogen. The mixture was stirred at this temperature for 1 hour. Methyl iodide (3.72 g, 0.026 mol) was added through a syringe maintaining temperature below −30° C. The mixture was further stirred at −40 to −45° C. for 1 hour and the reaction was quenched by the addition of water (50 ml). The layers were separated and the aqueous layer was extracted with ethyl acetate (50 ml×2). The combined organic phase was washed with pre-cooled 2N hydrochloric acid (25 ml) and finally with water (30 ml). The organic layer on concentration gave an oil which on crystallization from ethylacetate/hexane afforded a crude solid. It was further purified from methanol/water to yield the titled compound (VIIc) (7.5 g, 72% yield) in 99.37% purity (HPLC); m.pt.=148.5–150° C. (uncorrected).

$^1$H NMR (CDCl$_3$); δ 0.80–0.89 (m, 2-Me), 1.07–1.12 (m, 3-Me), 1.30–1.33 (d,1-Me), 1.87–1.94 (m, 6H) 2.2–2.3 (m,3H), 2.59–2.60 (m,2H), 3.85 (m, 1H), 4.46–4.48 (m, 1H), 5.36 (s, 1H), 5.5 (s, 1H), 5.74–5.80 (m, 1H), 5.97–6.0 (m, 1H), MS m/z: 433.5, 317.2 (M−116), 299.3 (317.2−18), 281.3 (299.3−18) IR (KBr pellet): ν max 3485, 2980, 1760, 1490, 1260, 850 cm$^{-1}$.

EXAMPLE 2

6(R)-[2-[8(S)-[[2,2-Dimethylbutanoyl]oxy]-2(S),6(R)-dimethyl-1,2,6,7,8,8a(R)-hexahydro-1(S)-napthyl]ethyl]-3(R)-methyl,4(R)-hydroxy-3,4,5,6-tetrahydro-2H-pyran-2-one (VIIa)

N-butyl lithium (1.6M, 23 ml, 0.036 ml) was added through a syringe into a solution of pyrrolidine (2.73 g, 0.038 mol) in THF (15 ml) at −30 to −25° C. under nitrogen. The mixture was stirred at −25° C. for 30 min. and a solution of simvastatin (5 g, 0.012 mol) was charged at −40° C. The mixture was stirred at −30° C. for about 1 hour and methyl iodide (5.12 g, 0.036 mol) was added. The mixture was further stirred at −30° C. for 1 hour and at −15° C. for 20 min. The reaction was quenched by the addition of water (30 ml). The layers were separated and the aqueous layer was extracted with ethyl acetate (20 ml). The combined organic phase was washed with 1N hydrochloric acid (30 ml), evaporated in vacuo to give an oil (4.2 g). It was found to be a mixture of (VIIa) and (VIIc) in 1:5 ratio, respectively as determined by HPLC. Isomer (VIIa) (500 mg) was isolated in pure form (99%) from the mixture using preparative HPLC.

While the present invention has been described in terms of its specific embodiments, certain modifications and equivalents will be apparent to those skilled in the art and are intended to be included within the scope of the present invention.

What is claimed is:

1. A compound having the structure of Formula VII:

FORMULA-VII

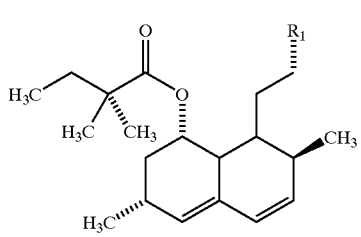

wherein R$_1$ is a β-hydroxypyranone ring of structural formulae VIIa–d

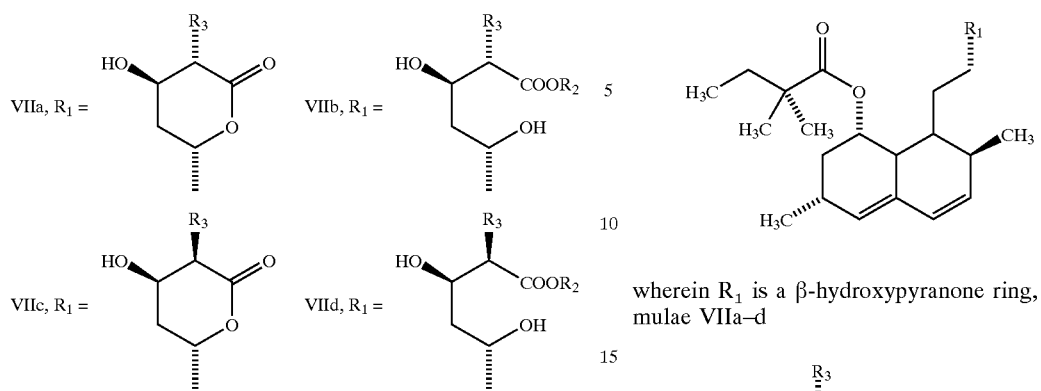

wherein $R_2$ is Na, K, or $NH_4$; and $R_3$ is a methyl group, and its pharmaceutically acceptable salts.

2. A method of treating hypercholesterolemia in a patient in need of such treatment which comprises administration of an antihypercholesterolemic effective amount of a compound having the structure of Formula VII:

FORMULA-VII

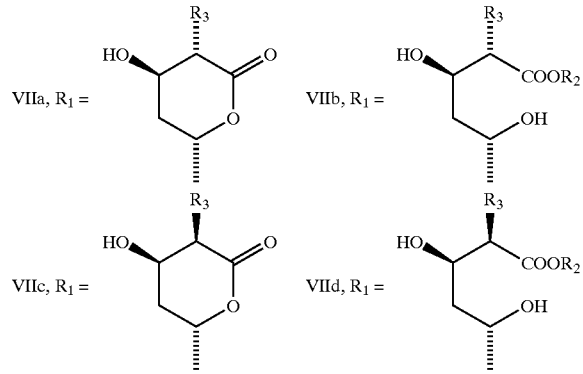

wherein $R_1$ is a β-hydroxypyranone ring of structural formulae VIIa–d

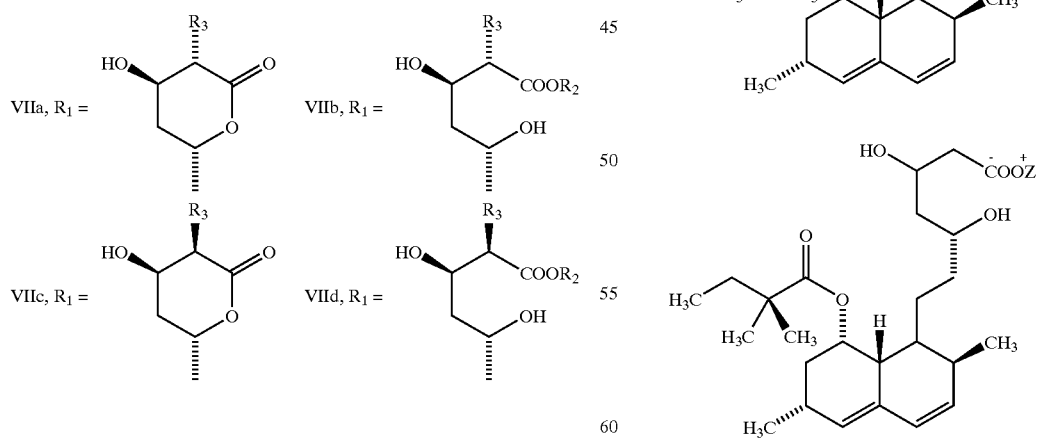

wherein $R_2$ is Na, K, or $NH_4$; and $R_3$ is a methyl group, and its pharmaceutically acceptable salts.

3. A process for the preparation of a compound having the structure of Formula VII

FORMULA-VII

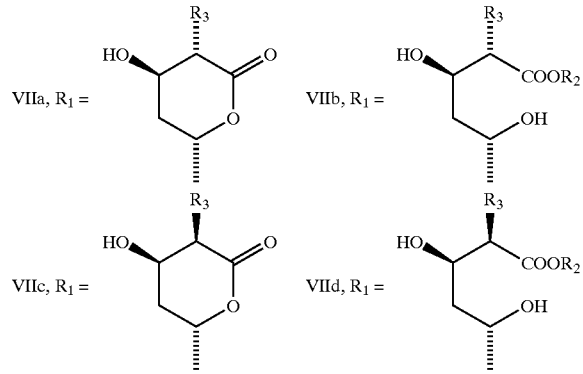

wherein $R_1$ is a β-hydroxypyranone ring, of structural formulae VIIa–d

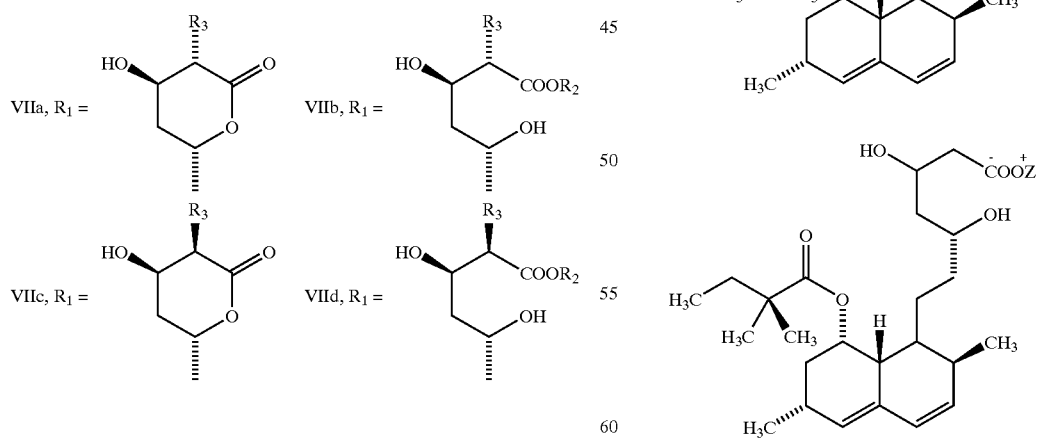

wherein $R_2$ is Na, K, or $NH_4$; and $R_3$ is a methyl group, which comprises reacting simvastatin of Formula VIIIa or VIIIb FORMULA-VIIIa

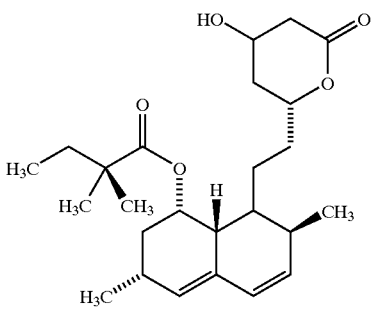

FORMULA-VIIIb

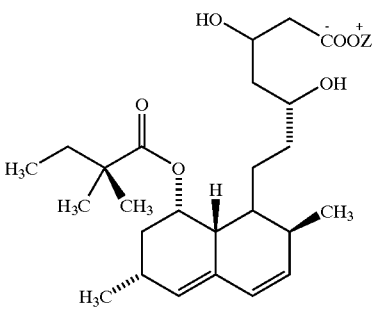

wherein Z is hydrogen, a metal cation, such as Na, K or $NH_4$, with a methylating agent.

4. The process of claim 3 wherein the reaction is performed without protecting the two hydroxy groups of the open pyranone ring of simvastatin.

5. The process of claim 3 wherein the methylating agent is methyl iodide.

6. The process of claim 3 wherein the reaction is carried out in the presence of a base.

7. The process of claim 6 wherein said base is lithium pyrrolidide or lithium hexadimethyldisilazane.

8. The process of claim 3 wherein the reaction is carried out at a temperature from about −10° to about −60° C.

9. The process of claim 8 wherein the temperature range being from about −25° C. to about −55° C.

10. The process of claim 3 further comprises suitable aqueous work up after the reaction is complete.

11. The process of claim 10 wherein said work up includes extraction with an organic solvent.

12. The process of claim 11 wherein the organic solvent is water—immiscible or partially miscible with water.

13. The process of claim 12 wherein the organic solvent is selected from the group consisting of choloroform, dichloromethane, 1,2-dichloroethane, hexanes, cyclohexane, toluene, methyl acetate or ethyl acetate.

14. The process of claim 11 further comprises adding a polar solvent after said extraction with an organic solvent.

15. The process of claim 14 wherein the polar solvent is a lower alkanol, ketone, ester, and mixtures thereof.

16. The process of claim 15 wherein the solvent is selected from the group consisting of methanol, ethanol, denatured spirit, isopropanol, acetone, methyl acetate, ethyl acetate, and mixtures thereof.

17. The process of claim 14 wherein the polar solvent is added after said extraction with an organic solvent and after the amount of the organic solvent has been reduced.

18. The process of claim 14 further comprises adding an anti-solvent to the polar solvent after said extraction with an organic solvent.

19. The process of claim 18 wherein the anti-solvent is at least partially miscible.

20. The process of claim 19 wherein the anti-solvent includes water, alkanes, mixture of alkanes, ethers or aromatic hydrocarbons.

21. The process of claim 20 wherein the anti-solvent is selected from the group consisting of hexane, cyclohexane, cyclopentane, isopropyl ether, benzene or toluene.

22. The process of claim 3 further comprising purifying the compound obtained by recrystallization from solvent(s).

* * * * *